(12) United States Patent
Gupta et al.

(10) Patent No.: US 7,882,726 B2
(45) Date of Patent: Feb. 8, 2011

(54) COMPRESSION VACUAPORE FOR DETERMINATION OF PORE STRUCTURE CHARACTERISTICS OF HYDROPHOBIC MATERIALS UNDER COMPRESSIVE STRESS

(75) Inventors: Krishna M. Gupta, Ithaca, NY (US); Akshaya Jena, Ithaca, NY (US)

(73) Assignee: Porous Materials, Inc., Ithaca, NY (US)

( * ) Notice: Subject to any disclaimer, the term of this patent is extended or adjusted under 35 U.S.C. 154(b) by 342 days.

(21) Appl. No.: 11/954,035

(22) Filed: Dec. 11, 2007

(65) Prior Publication Data

US 2008/0276690 A1 Nov. 13, 2008

Related U.S. Application Data

(60) Provisional application No. 60/916,800, filed on May 8, 2007.

(51) Int. Cl.
*G01N 15/08* (2006.01)
(52) U.S. Cl. .......................................................... 73/38
(58) Field of Classification Search ...................... 73/38
See application file for complete search history.

(56) References Cited

U.S. PATENT DOCUMENTS

| | | | |
|---|---|---|---|
| 2,705,418 A | 4/1955 | Reichertz et al. | |
| 2,706,904 A | 4/1955 | Hertel | |
| 3,216,242 A | 11/1965 | Eyrich | |
| 3,577,767 A | 5/1971 | Stedile | |
| 5,394,737 A | 3/1995 | Prange | |
| 5,512,600 A * | 4/1996 | Mikos et al. ................ | 523/113 |
| 6,178,808 B1 | 1/2001 | Wang | |
| 6,242,539 B1 * | 6/2001 | Tadokoro et al. ............ | 525/358 |
| 6,655,192 B2 * | 12/2003 | Chavdar ....................... | 73/38 |
| 6,684,685 B2 * | 2/2004 | Gupta et al. .................. | 73/38 |
| 7,210,335 B2 | 5/2007 | Gupta | |

FOREIGN PATENT DOCUMENTS

JP    02268249    11/1990

* cited by examiner

*Primary Examiner*—Hezron Williams
*Assistant Examiner*—Alex Devito
(74) *Attorney, Agent, or Firm*—Thomas T. Aquilla

(57) ABSTRACT

A method for determining pore structure characteristics of hydrophobic porous materials includes placing a test sample of material in the sample chamber of a porosimetry apparatus, creating a partial vacuum and evacuating the sample chamber to remove air, creating a partial vacuum and evacuating the penetrometer and storage vessel above the water level, releasing the vacuum in a controlled manner, so pressure is applied and water in the penetrometer enters the sample chamber and intrudes into pores of the sample, applying a measured amount of intrusion pressure and measuring the change in volume of water in the penetrometer, and determining pore structure characteristics of the sample based on the change in volume of water in the penetrometer. The method further includes an optional step of applying a desired amount of compressive stress on the sample prior to testing. Nonporous plates optionally are used to measure x-y plane pore structure.

17 Claims, 1 Drawing Sheet

COMPRESSION VACUAPORE FOR DETERMINATION OF PORE STRUCTURE CHARACTERISTICS OF HYDROPHOBIC MATERIALS UNDER COMPRESSIVE STRESS

REFERENCE TO RELATED APPLICATIONS

This application claims an invention, which was disclosed in Provisional Application No. 60/916,800, filed May 8, 2007, entitled "METHOD AND APPARATUS FOR DETERMINATION OF DIAMETER, VOLUME, AND DISTRIBUTION OF PORES IN HYDROPHOBIC MATERIALS". The benefit under 35 U.S.C. §119(e) of the United States Provisional Application is hereby claimed, and the complete disclosure of the aforementioned application is hereby incorporated herein by reference in its entirety.

BACKGROUND OF THE INVENTION

1. Field of the Invention

The invention pertains to the field of pore structure characterization. More particularly, the invention pertains to a method and apparatus for determination of the diameter, volume and distribution of pores in hydrophobic porous materials.

2. Description of Related Art

Various porous materials currently are being developed and used for applications in a wide variety of industries, including, for example, fuel cells, biotechnology, filtration, and the household, hygienic and apparel industries, to name but a few. Many of these novel porous materials are hydrophobic in nature. These water repellent materials come with a wide range of pore sizes and physical characteristics. The pore structure characteristics of such materials, such as, for example, pore volume, pore diameter and pore distribution of the materials, often are required for a useful evaluation of the materials' quality and performance.

Many applications of such hydrophobic porous materials often require the materials to operate under compressive stress (e.g., filtration and fuel cells are common examples). Therefore, the influence of compressive stress on the pore structure characteristics of the porous materials often is required to evaluate the suitability of the materials for various applications. Thus, there is a strong need in the art for the development of suitable technology to measure the pore structure characteristics of hydrophobic materials, particularly while such materials are subjected to compressive stress. Pore structure characteristics in the x-y plane determine the performance of a number of materials in application. For example, in materials used in the manufacture of diapers, in-plane permeability and liquid intakes are important. Previously, there was no available technique for measurement of in-plane pore volume. Thus, there is a strong need in the art for the development of suitable technology to measure the pore structure characteristics of hydrophobic materials in the x-y plane.

U.S. Pat. No. 7,210,335 discloses an automated clamp-on sample chamber for flow porometry and a method of using same. The sample chamber includes a movable upper chamber. The movable upper chamber includes a center bore opening to a bottom of the chamber, at least one port for introduction of gas under pressure to the center bore, and a first annular seal around the center bore. A stationary lower seat opposing the upper chamber has a center bore aligned with the upper chamber, and includes an exhaust and a second annular seal around the center bore. A test material is placed between the upper chamber and the lower seat. An actuator moves the upper chamber. When the upper chamber is moved down with the first annular seal in contact with an upper surface of a sample of the material and the second annular seal in contact with a lower surface of the sample, gas introduced to the upper chamber goes through the sample and out through the exhaust. Measured differential pressures and gas flow rates yield pore diameter, pore distribution, and permeability.

U.S. Pat. No. 6,655,192 discloses a permeameter-porosimeter for providing normal and lateral permeability measurements on porous materials. The permeability measurements can be made on compressed or uncompressed samples and can be made at room temperature or at elevated temperatures. A wide variety of fluids, gas or liquid, can be used as the penetrating test fluid, depending on the application and the porosity of the porous sample. The penetrating test fluid is forced through the sample under pressure. The load, the fluid displacement, and the time are recorded and used in the calculations of permeability, porosity, pore size distribution, average pore size and the number of pores per unit area.

U.S. Pat. No. 6,178,808 discloses a method for measuring hydraulic conductivity of geological samples, using a closed volume pumping system that ensures constant volume of test liquid within the sample, and a shaped tube of mercury to provide a constant pressure difference across the sample to eliminate second order influences on the hydraulic conductivity measurement and to speed measurement.

U.S. Pat. No. 5,394,737 discloses an apparatus for testing the permeability of shredded elastomeric material, which contains a vessel, a bed of tire chips in the vessel, and a fluid inlet which communicates with a first fluid outlet and a second fluid outlet through the bed of tire chips. The first fluid outlet is provided with a cap for optionally preventing fluid flow through it. The second fluid outlet is higher than both the fluid inlet and the first fluid outlet. A plate located above the bed of tire chips is used to compress the tire chips.

U.S. Pat. No. 3,577,767 discloses a felt permeability testing apparatus. Various permeability characteristics of a sample of felt or other permeable web materials are determined by testing apparatus comprising a pair of interchangeable platens between which the sample is subjected to controlled compression, as a measured flow of liquid is forced through the sample from one platen to the other, along a predetermined flow path established by the particular pair of platens installed in the apparatus.

Japanese Patent Publication No. 02268249 discloses a water permeability testing method to facilitate the computation of water permeability coefficients in a short time, by laminating a sample to be measured with measuring samples whose permeability coefficients are larger than that of said sample, forming a test body, making water permeate into the test body, and measuring a unit quantity of permeation. A test body having a laminated structure is formed on a stage seat at the bottom of a pressure-proof container with the following materials: a sample to be measured whose thickness is thin and permeability coefficient is unknown, and measuring materials whose permeability coefficients are known and larger than that of the sample. Then water is infiltrated into the test body from a water feeding tank. The unit quantity of water permeation in a measuring buret is measured through a water pipe. The unit quantity of water permeation, the unit cross sectional area of the test body and a unit hydraulic grade are substituted for the terms of the equation of Darcy's law. Thus the permeation coefficient of the entire test body is computed. Then, the permeation coefficient of the sample to be measured is obtained, based on the permeation coefficient and the thickness of the entire test body, the thickness of the sample to be measured and the permeation coefficients of the measuring materials.

Mercury intrusion porosimetry is a well known technique widely used to measure pore size, pore volume, and pore volume distribution of porous materials, which are not wetted by mercury. In this technique, mercury is allowed to surround the non-wetting sample. The non-wetting mercury does not enter the pores of the sample spontaneously, rather, application of pressure on the mercury forces it to intrude into the pores of the sample.

The pressure required for intrusion of the non-wetting mercury into a pore is related to the diameter of the pore and is given by the following well known relation:

$$(P-P_p)=-4\gamma \cos\theta/D \tag{1}$$

where P is the intrusion pressure on the non-wetting mercury, $P_p$ is the gas pressure in the pore, $\gamma$ is the surface tension of the non-wetting mercury, $\theta$ is the contact angle of the non-wetting mercury with the sample, and D is the pore diameter.

The intrusion pressure is positive because the contact angle, $\theta$, of a non-wetting liquid is greater than 90° and cos $\theta$ is negative. With increasing pressure, intrusion occurs into smaller pores. Intrusion pressures and intrusion volumes are then measured. Intrusion pressure gives pore diameter. At a given intrusion pressure, all pores larger than the pore corresponding to the intrusion pressure are filled with mercury. The intrusion volume at the intrusion pressure is the volume of all pores filled with mercury at the intrusion pressure.

The surface tension of mercury is 480 dynes/cm and the contact angle is 140°. The sample is evacuated before mercury surrounds the sample. Therefore, the pore diameter is computed taking $P_p$ as zero. Typical differential pressures required to measure pore structure characteristics by mercury intrusion and water intrusion are shown in Table 1.

TABLE 1

| Pore diameter (μm) | Differential Pressure of Mercury on pores (psi) | Differential Pressure of Water on pores (psi) |
| --- | --- | --- |
| 0.001 | 213,000 | 20,900 |
| 0.005 | 42,700 | 4,180 |
| 0.010 | 21,300 | 2,090 |
| 0.100 | 2,130 | 209 |
| 1 | 213 | 20.9 |
| 10 | 21.3 | 2.09 |
| 20 | 10.7 | 1.04 |
| 50 | 4.27 | 0.418 |
| 100 | 2.13 | 0.209 |
| 200 | 1.07 | 0.104 |

Mercury intrusion porosimetry has a number of limitations. For example, the intrusion pressures for mercury intrusion are very high, particularly for small pores. High pressures tend to distort the pore structure and provide less reliable pore size distribution data. The large pores also are difficult to measure accurately, because the small pressures required are difficult to control accurately in the wide pressure range normally employed for the test, and further, because of the high density of mercury, large pores may get filled up due to pressure created by gravity. In-plane pore structure can not be measured by mercury intrusion porosimetry. Moreover, the effect of compressive stress on the sample on its pore structure cannot be determined by mercury intrusion porosimetry. Furthermore, mercury used in the test is toxic and is forbidden in many work environments. The sample also gets contaminated with mercury, cannot be reused, and must be properly disposed. Because of such limitations of this technique, mercury intrusion porosimetry is not effective in determining the pore structure characteristics of many materials of interest.

Water Intrusion Porosimetry is another known technique. Water does not enter the pores of hydrophobic materials spontaneously, rather, on application of pressure on water it enters the pores. In this technique, pressure is increased on water surrounding the sample. Intrusion pressures and intrusion volumes are measured. Intrusion pressure gives pore diameter. At a given intrusion pressure, all pores larger than the pore corresponding to the intrusion pressure are filled with water. The intrusion volume at the intrusion pressure is the volume of all pores filled with water at the intrusion pressure. The surface tension of water is 72 dynes/cm and the contact angle is often 120°. The sample is not evacuated before surrounding with water because of evaporation of water. The pore diameter is computed neglecting the pressure of gas in the pore, $P_p$ and using the following relation, already cited above, and:

$$(P-P_p)=-4\gamma \cos\theta/D \tag{2}$$

where P is the intrusion pressure on the non-wetting water, $P_p$ is the gas pressure in the pore, $\gamma$ is the surface tension of the non-wetting water, $\theta$ is the contact angle of water with the sample, and D is the pore diameter. Typical pressures required for intrusion of water into the pores of hydrophobic materials are listed in Table 1.

However, as with mercury, the available technology for water intrusion porosimetry also has a number of limitations and disadvantages. Using the available technology for water intrusion porosimetry, pore structures of samples under compressive stress cannot be determined. Currently known methods for water intrusion porosimetry also cannot measure volume and diameter of pores in the x-y plane.

Another disadvantage of water intrusion porosimetry is that the air trapped in a pore prevents water from completely filling the pore. Thus, the pore volume occupied by the trapped air is not measured. Because of the relatively high pressure of the trapped air, a large part of the pore volume is not measured in large and small pores, and part of the pore volume of large pores is measured at much higher pressures. Furthermore, because of the pressure of the gas trapped inside the pores, higher differential pressure is needed for intrusion. Therefore, the computed pore diameter is less than the actual pore diameter. Although the error in the measured pore diameter generally is negligible for small pores, it is very high in the case of large pores, because of large relative pressures of the trapped air.

Yet another disadvantage of water intrusion porosimetry is that, when water surrounds the sample in the sample chamber for intrusion, the air present in the sample chamber is trapped in the sample chamber above the water. This air does not dissolve in the already air-saturated water. When the pressure of the water is increased for intrusion, the air trapped in the sample chamber is compressed. Water fills the space created by the decrease in volume of the trapped air in the sample chamber, due to compression of the trapped air, and the intrusion volume of the water is measured as the pore volume. This error can be appreciable for large and small pores, although part of it can be compensated by a blank run. In a blank run, the intrusion volume is measured as a function of differential pressure, without the sample, and the measured intrusion volume is subtracted from the measured intrusion volume of the sample. This procedure also corrects for errors due to the effect of compressibility of the liquid and expansion of the sample chamber. However, such corrections can be cumbersome and can introduce a significant source of error.

Hence, although there are known methods and apparatus that are intended to aid in the analysis of the pore structure characteristics of various porous materials, one problem with the known methods is that they are not well-suited for accurately analyzing the pore volume and pore diameter of hydrophobic porous materials, they are incapable of measuring pore volume and diameter of hydrophobic materials under compressive stress, and incapable of evaluating the pore volume and diameter of in-plane pores. Thus, there is a continuing need in the art for a method and apparatus suitable for accurately measuring the pore volume and diameter of hydrophobic materials under compressive stress and in the in-plane.

SUMMARY OF THE INVENTION

The present invention provides a novel technology for water intrusion compression porosimetry, suitable for accurate pore structure characterization of hydrophobic materials under compressive stress and in the in-plane, and having none of the disadvantages of the prior art technology for water intrusion porosimetry.

Briefly stated, the invention provides a method and apparatus for using water intrusion compression porosimetry for accurate pore structure characterization of hydrophobic materials. The unique design of the invention permits a porous test sample to be kept under the desired compressive stress during water intrusion. In the preferred embodiment, the sample chamber has a screw-on lid with an O-ring seal. The sample is held between two rigid plates with large holes. The bottom plate is placed on the corrugated bottom of the sample chamber. The top plate is connected to a rod that passes through a pressure-tight seal in the lid and is linked to a piston-cylinder device pneumatically operated for accurately applying controlled compressive stress on the sample. This arrangement permits the sample to be kept under the desired compressive stress of zero or higher, and permits intrusion of water into the pores of the sample from all sides. Another feature of the unique design of the invention is the ability to independently evacuate the sample chamber and the space above water in the penetrometer and the storage chamber. The sample chamber can be evacuated to any desired vacuum without evaporating water.

In one embodiment, the invention provides apparatus for the analysis of pore structure characteristics of porous materials, including a sample chamber having a corrugated bottom and a closure or lid having a mechanism for creating a pressure-tight seal between the sample chamber and the lid, a sample holding mechanism within the sample chamber, having top and bottom opposing rigid plates with holes arranged through their opposing surfaces, a penetrometer connected to the sample chamber, the penetrometer including a water reservoir and a mechanism for measuring a change in volume of the water, a gas line for supplying an inert gas at an adjustable controlled pressure for pressurization of water within the penetrometer, a vacuum line for creating a partial vacuum within the sample chamber, penetrometer and storage vessel, and preferably a mechanism for accurately applying compressive stress on the sample. In yet another unique embodiment, the sample is sandwiched between two rigid nonporous plates having no holes. In this method, the water intrudes the sample only radially along its x-y plane. Therefore, pore structure characteristics of radial pores are evaluated.

In another embodiment, the invention provides a method for determining pore structure characteristics of a hydrophobic porous material, including the steps of providing a suitable water intrusion compression porosimetry system, placing a test sample of a porous hydrophobic material between the top and bottom opposing rigid plates, placing the bottom plate on the corrugated bottom of the clean sample chamber, sealing the pressure-tight seal between the sample chamber and the closure or lid, creating a partial vacuum and evacuating the sample chamber to remove air from the sample chamber, creating a partial vacuum and evacuating the penetrometer and storage vessel above the water level, releasing the vacuum in a controlled manner, such that pressure is applied and water contained in the penetrometer enters the sample chamber and intrudes into the pores of the sample, applying a measured amount of intrusion pressure and measuring the change in volume of water in the penetrometer, and determining one or more pore structure characteristics of the sample based on the change in volume of the water in the penetrometer. The method further includes an optional step of applying a desired amount of compressive stress on the sample prior to testing. The compressive stress optionally is zero or any higher desired value.

The invention provides the unique advantage of enabling the analysis of pore structure characteristics of hydrophobic materials under compressive stress, using a novel technique of water intrusion compression porosimetry, which previously was unavailable.

These and other features and advantages will become readily apparent from the following detailed description, which should be read in conjunction with the accompanying drawing figures.

BRIEF DESCRIPTION OF THE DRAWING

The drawing figures are not necessarily to scale, with the emphasis instead placed upon the principles of the present invention. Additionally, each of the embodiments depicted are but one of a number of arrangements possible utilizing the fundamental concepts of the present invention. The drawings are briefly described as follows.

DETAILED DESCRIPTION OF THE INVENTION

Figure 1:
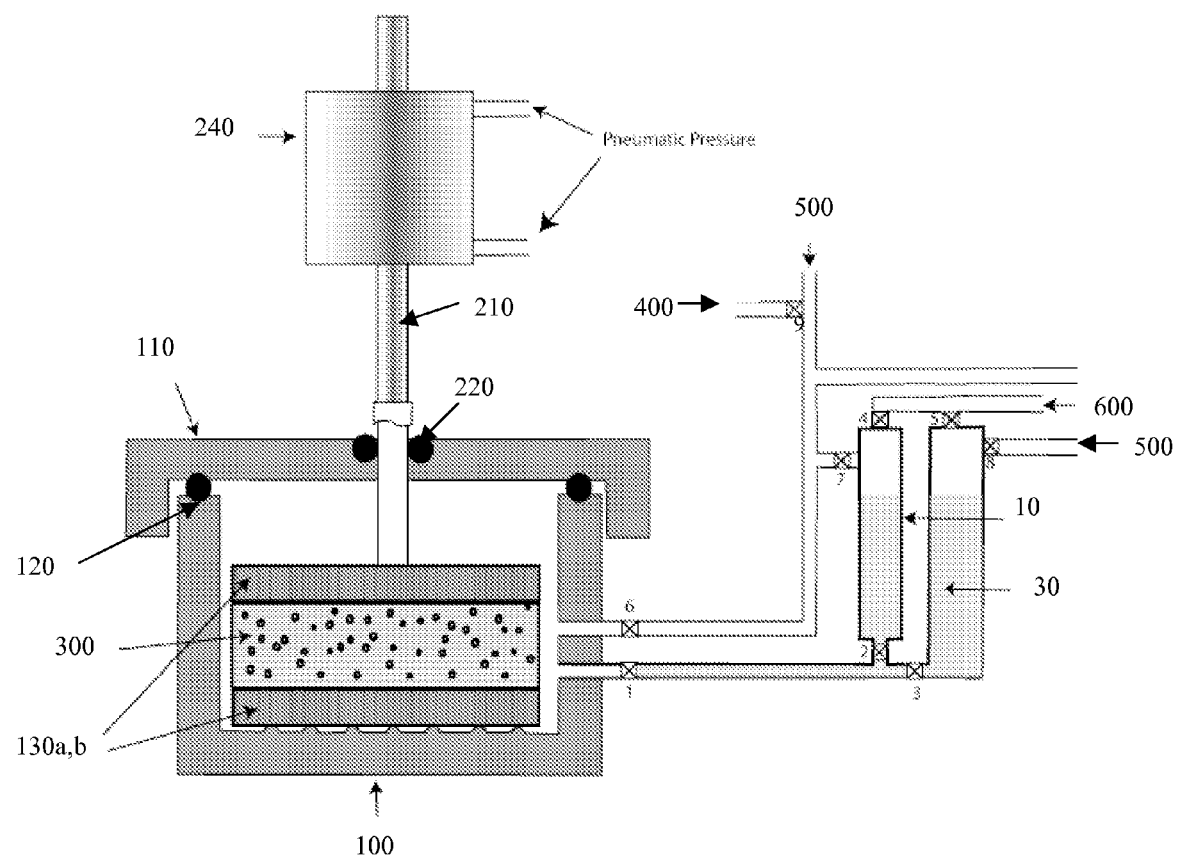
FIG. 1 shows a porosimetry system suitable for determination of pore structure characteristics of hydrophobic materials in accordance with an embodiment of the present invention.

The following description relates to certain preferred embodiments of an apparatus and method for using water intrusion compression porosimetry to determine the pore structure characteristics of hydrophobic porous materials, even while the porous materials are subjected to compressive stress. Numerous variations and modifications, other than those specifically indicated herein, will be readily apparent to those of sufficient skill in the art. In addition, certain terms are used throughout the discussion in order to provide a convenient frame of reference with regard to the accompanying drawings, such as "top", "bottom", and the like. However, such terms are not intended to be specifically limiting of the invention, except where so indicated in the claims.

The invention provides novel technology for using water intrusion compression porosimetry for accurate pore structure characterization of hydrophobic materials under compressive stress, overcoming the disadvantages of the available technology currently used for water intrusion porosimetry. The unique design of the invention permits a porous test sample to be kept under the desired compressive stress during water intrusion. Water intrusion porosimetry is an ideal test for hydrophobic materials. For example, the intrusion pressure is low and the sample can be salvaged and reused. Characterization of hydrophobic pores in a mixture of hydrophobic and hydrophilic pores also can be determined using this method. Furthermore, the equipment is simple, inexpensive and almost maintenance-free.

Referring now to FIG. 1, a porosimetry system suitable for determination of pore structure characteristics of hydrophobic porous materials in accordance with an embodiment of the present invention is shown. The sample chamber 100 has a closure 110, which preferably is a screw-on lid having an O-ring seal 120. The porous material test sample 300 is held between two rigid plates 130a,b having relatively large holes (about one mm diameter) arranged through their opposing surfaces. The hole density is such that the holes constitute about fifty percent of the volume of each plate. The holes permit entry of water from the top and bottom of the sample. The bottom plate is placed on the corrugated bottom of the sample chamber 100. The corrugated bottom plate permits easy entry of water. The top plate is connected to a rod 210 that passes through a vacuum seal 220 in the lid 110 and is linked to a piston-cylinder device 240 pneumatically operated for accurately applying controlled compressive stress on the sample. This arrangement permits the sample to be kept under the desired compressive stress of zero or higher, and permits the intrusion of water into the pores of the sample from all sides.

The sample chamber 100 is operably connected to a penetrometer 10 through valve 1 and valve 2. The penetrometer is filled with water from a water reservoir 30 connected to the penetrometer through valve 3. The penetrometer 10 and water reservoir 30 are operably connected through valve 4 and valve 5 respectively to a gas line 600 capable of supplying an inert gas at an adjustable controlled pressure for pressurization of the water. Water pressurized in the penetrometer enters the sample chamber. The water in the reservoir is pressurized to refill the penetrometer.

The sample chamber 100 further is operatively connected to a vacuum line 500 through valve 6, for evacuation of the sample chamber 100. The vacuum line 500 is also operatively connected to the penetrometer 10 through valve 7, and to the water storage vessel 30 through valve 8, for evacuation of the penetrometer and water storage vessel above the water level. A vent 400 is provided in the vacuum line 500 through valve 9.

For evaluating a sample porous material, the test sample 300 is loaded into the clean sample chamber 100, between rigid plates 130a and 130b, and the sample chamber cap 110 is sealed.

The sample chamber is evacuated, preferably to at least 1 torr. Air pressure is used to actuate the piston-cylinder device 240 to apply the desired compressive stress through rod 210, which forces the porous rigid plates 130a and 130b to transmit the desired pressure to the test sample, thereby loading the desired compressive stress on the sample. The penetrometer and storage vessel are evacuated above the water level, optionally to about 20 torr. A vacuum regulator is used for controlled release of vacuum above the penetrometer, so that small desired sub-atmospheric pressures on the water in the penetrometer can be accurately created for measurement of large pores. Any one of the commercially available vacuum regulators can be used for creating sub-atmospheric pressures. In other words, increasing pressure is applied to the sealed test system by controlled incremental release of the partial vacuum previously applied to the penetrometer. The water reservoir is used to refill the penetrometer whenever it is required. Evacuation also causes evaporation of water for maintaining equilibrium vapor pressure at the test temperature. The equilibrium vapor pressure of water at the typical test temperature of 18° C. is 0.3 psi. Therefore, evacuation above water can be done down to 20 torr (0.39 psi), as explained in further detail below.

The sample chamber 100 is operably connected to penetrometer 10 through valve 1 and valve 2, such that, upon application of pressure on the water in the penetrometer, the pressurized water contained in the penetrometer enters the sample chamber and intrudes into the pores of the sample. A measured amount of intrusion pressure is applied, the change in the volume of water in the penetrometer is measured, and the decrease in the volume of water in the penetrometer is the calculated cumulative pore volume.

For measuring the change in the volume of the water, a water level sensing device (NOT SHOWN) is attached to the penetrometer. Several techniques for sensing the water level optionally are used. For example, the sensing of displacement of a magnet floating on water in the penetrometer yields the change in volume of water in the penetrometer. Alternatively, a change in the capacitance of the penetrometer column is also used as a measure of the change in the volume of water in the penetrometer. Alternatively, any known method for measuring the change in the water volume can be used.

In an alternative embodiment, for evaluation of pore structure characteristics of radial pores, the sample is sandwiched between two rigid nonporous plates having no holes. The compressive stress optionally can be zero or any higher desired value. In this method, the water intrudes the sample only radially along its x-y plane. Thus, pore structure characteristics of radial pores can be evaluated.

Very small intrusion pressures are required for water intrusion. For example, a 20 micron pore requires only about one psi for intrusion to occur. Therefore, in order to create small sub-atmospheric pressures on water, the following special innovative technique is used. The penetrometer and storage vessel are evacuated above the water level. A vacuum regulator is used to control pressure. The regulator increases pressure by controlled release of the vacuum and maintains pressure at any set value below atmospheric pressure. In this manner small desired pressures on water are accurately created. Evacuation of the penetrometer and storage vessel causes evaporation of water for maintaining equilibrium vapor pressure at the test temperature. The equilibrium vapor pressure of water at a typical test temperature of 18° C. is 0.3 psi. Therefore, evacuation to 20 torr (0.39 psi) generally is considered adequate. A measured amount of intrusion pressure is then applied and the change in volume of the water in the penetrometer is measured. The decrease in the volume of the water in the penetrometer is the cumulative pore volume.

Another unique feature of the invention is that the sample chamber is evacuated in order to remove air from the sample chamber. With the previously known techniques, any air left in pores creates back-pressure and reduces the applied pressure by an uncertain amount. With the prior art techniques, this error becomes prohibitive for the small intrusion pressures required by large pores. Using the apparatus shown in FIG. 1, easy evacuation of the sample chamber 100 is possible, because of the holes in the plates (130a,b) sandwiching the sample and the corrugated bottom of the sample chamber. A sample chamber vacuum of 1 torr (0.019 psi) is considered adequate for accurate measurement of large pores. However, the same amount of vacuum above the water column and in the sample chamber optionally can be used.

When water at 0.39 psi is allowed to enter the sample chamber at a much lower pressure of 0.019 psi (1 torr), water rushes into the sample chamber to surround the sample and the pressure of the gas inside the sample chamber increases as the gas is compressed. Insufficient time is available for the trapped air to dissolve in the water and for the water to evaporate to maintain its equilibrium vapor pressure. Thus, when the water completely covers the sample, the gas in the pores gets trapped. The pressure of the air trapped in the pores is given by the following relation:

$$P_p = Pv[Vsc-Vbs+V_p]/[(Vsc-Vbs)f+V_p] \quad (3)$$

where $P_p$ is the pressure of the gas trapped in the pores, Pv is the air pressure left in the sample chamber after vacuum, Vsc is the volume of the sample chamber, Vbs is the volume of bulk sample, $V_p$ is the volume of pores, and f is the fraction of (Vsc–Vbs) filled by water for covering the sample completely.

If 50% of the space between the sample and the sample chamber is filled with water for covering the sample completely, then (f=0.5) and Pv=0.019 psi, so $P_p$ is about 0.038 psi. Thus, the pressure of the gas trapped in the pores is about 0.038 psi. As the water continues to enter the sample chamber and reaches its pressure of 0.39 psi, the air trapped outside the pores is compressed to 0.39 psi. Thus, the air trapped in 50% of (Vsc–Vbs) at 0.038 psi will occupy a volume, which is only 4.9% of (Vsc–Vbs).

When the pressure on the water is increased for intrusion, the trapped air influences the measured pore diameter and intrusion volume (pore volume) in several ways. The intrusion pressure increases slowly from 0.39 psi. If the intrusion pressure is 1 psi (P=1 psi) for pores of about 20 microns in diameter, the differential pressure on the pores is [P–$P_p$] ($P_p$=0.038 psi). D(P=1 psi)=20.9 μm when $P_p$ is ignored and D(P=1-0.038=0.962 psi)=21.7 μm, when the pressure of the gas trapped in the pores is taken into consideration. The difference is small for the large pore sizes. For smaller pore sizes, the pressure of the trapped gas is negligible, compared with the much higher pressure required for smaller pore sizes. Thus, the total effect of trapped air on the measured pore diameters of small as well as large pores is small, due to performing the evacuation step.

Trapped air influences the measured pore diameter and intrusion volume (pore volume) in other ways as well. As intrusion of water into a pore continues, the air trapped in the pore is compressed, its pressure increases, and higher differential pressure becomes necessary for further intrusion. For example, when trapped air at 0.038 psi is compressed to 10% of the volume of a pore, its pressure increases to 0.38 psi, and further intrusion requires 0.38 psi additional pressure. The higher intrusion pressure yields a smaller calculated pore diameter. Thus, a cylindrical pore will be measured as a slightly conical inverted pore. However, because of the small pressure of the trapped air, the effect is small for large pores and negligible for small pores.

Furthermore, the pore volume occupied by trapped air in a pore will be measured only when the trapped air in the pore is compressed to a negligible volume at high pressures, which correspond to smaller pores. Therefore, a small part of the volume of larger pores will be measured as the volume of smaller pores.

When the pressure of the water is increased beyond 0.39 psi, the air trapped above the water in the sample chamber is compressed. For example, when the pressure on water is increased from 0.39 psi to 1 psi, the decrease in volume of air is 3% of (Vsc–Vbs). This decrease in the volume of the trapped air in the sample chamber is occupied by water and is measured as the pore volume. (Vsc–Vbs) is normally a few tenths of a cm3. Thus, the error of about 0.005 cm3 is small. This error is greater at higher intrusion pressures. Fortunately, most of this error can be eliminated by blank runs.

Because the water used for intrusion is evacuated, the water is unsaturated with air. The air trapped in the pores as well as in the sample chamber gradually dissolves in the unsaturated water. Dissolution of trapped air reduces the pressure of the trapped air in the pores and further reduces the small errors in the measured pore diameters, the conical effect on pore shape, and the shifting of pore volume to smaller pore sizes. The dissolution of trapped air above water in the sample chamber reduces the volume by which the trapped air will be compressed and thus reduces the error in the measurement of pore volume.

Water tends to evaporate in order to approach its equilibrium vapor pressure, but evaporation is a slow process. If sufficient time is allowed, water will evaporate and try to maintain its equilibrium vapor pressure (0.3 psi at 18° C.) above the water in the sample chamber and inside the pores. Because sufficient time is provided, the trapped air completely dissolves in the water. Thus, there is no vapor or air above the water in the sample chamber at even the initial pressure of 0.39 psi. The air trapped in the pores dissolves and water tends to evaporate in order to maintain its equilibrium vapor pressure inside the pores. However, evaporation inside pores is a very slow process. If sufficient evaporation has not occurred, the pressure of the gas in the pores is negligible and there is no effect on pore diameter or pore volume. If, however, water is able to maintain its vapor pressure inside the pores, then the vapor pressure would depend upon the pore diameter and each pore would have a fixed pressure, which does not change with extent of intrusion into the pore. If the vapor pressure in a pore is Pw, then the pore diameter is given by the well-defined differential pressure (P–Pw). Thus pore diameter is well defined. However, Pw is negligible compared with P in the case of small pores. Other errors, such as conical effect on pore shape and shifting of pore volume to smaller pore sizes, are fully eliminated.

Intrusion Pressure—The sample chamber, penetrometer and water storage vessel are evacuated. The pressure in the pores and the initial intrusion pressures are close to the vapor pressure 0.3 psi of water at the test temperature of 18° C. Even if the pressure in the sample chamber is <0.3 psi, water will tend to maintain a vapor pressure of 0.3 psi. Consequently, the following equation:

$$(P-P_p) = -4\gamma \cos \theta / D \quad (4)$$

where $P_p = p_g = 0.3$ psi, and the surface tension of water is 72 dynes/cm. The contact angle of water can vary appreciably in different materials, depending upon the degree of hydrophobicity. However, the contact angle of water for many materials is close to 120°.

The intrusion pressures of water and the measurable pore diameters at various intrusion pressures are listed in Table 2. The results show that the method of the present invention requires small intrusion pressures and can accurately measure small pore diameters. Furthermore, the present invention, unlike the prior art, can accurately measure the diameters of large pores as well.

TABLE 2

| Intrusion Pressure on water, P (psi) | Gas Pressure (0.3 psi) in Pore ($p_g$) (0.3 psi) relative to Intrusion Pressure, P(psi) | Pore diameter computed neglecting $p_g$ (μm) |
|---|---|---|
| 20,000 | Negligible | 0.001 |
| 10,000 | Negligible | 0.002 |
| 5,000 | Negligible | 0.004 |
| 2,000 | Negligible | 0.010 |
| 1,000 | Negligible | 0.021 |
| 100 | Negligible | 0.209 |
| 10 | Negligible | 2.088 |

TABLE 2-continued

| Intrusion Pressure on water, P (psi) | Gas Pressure (0.3 psi) in Pore ($p_g$) (0.3 psi) relative to Intrusion Pressure, P(psi) | Pore diameter computed neglecting $p_g$ (µm) |
|---|---|---|
| 5 | Negligible | 4.1276 |
| 1 | <30%* | 20.877 |

*Expected to be much less than 30% because evacuated and unsaturated water used for intrusion can absorb trapped air, and the short test duration is likely to prevent establishment of equilibrium vapor pressure of water.

Measurable Pore Structure Characteristics:

Through Pore and Blind Pore Volume—As in other porosimeters, the intrusion volume measured in the penetrometer apparatus of the present invention is the pore volume. The air trapped above the water in the sample chamber gets compressed with increased intrusion pressure. The reduction in the volume of the trapped air is measured as the pore volume and is an error. Part of this error can be eliminated by making use of a blank test. A blank test is a test in which the sample is not used. The pore volume measured in the blank test is subtracted from the pore volume measured in the test. In the apparatus shown in FIG. 1, the balance of this error is negligible, because there is very little air left in the sample chamber after evacuation, and the evacuated and unsaturated water used for intrusion absorbs any trapped air. Thus, the difficulties encountered with the prior art are eliminated.

Through Pore and Blind Pore Diameter—The pore diameter is computed using equation 3 shown in paragraph [0041]. The pressure in the pore, $P_p(p_g)$, used in this equation, will be equal to or less than the small pressure of the gas left in the pore after evacuation, because part of the air left in the pores will be absorbed by the intruding evacuated unsaturated water. Because of short test duration, water is unlikely to have sufficient time to evaporate and maintain its equilibrium vapor pressure in the pores. If water is able to main its equilibrium vapor pressure of 0.3 psi at 18° C. during the normally short test duration, the pressure of air in the pore, $p_g$, will be 0.3 psi. This small pressure is mostly negligible and pore diameters are accurately measured.

Through Pore and Blind Pore Volume Distribution—The through pore and blind pore volume distribution is given in terms of the distribution function, $f_v(\log D)$, defined in the following manner:

$$f_v(\log D) = -dV/d \log D \quad (5)$$

where V is the cumulative pore volume and D is the pore diameter. The area under the distribution function in any pore diameter range yields the volume of pores in that range.

The present invention thus provides the advantage of enabling the rapid and more accurate characterization of hydrophobic pore structure characteristics in the bulk material as well as in the x-y plane, hydrophobic pores in a mixture of hydrophilic and hydrophobic pores, and the effects of compressive stress on hydrophobic pores on a variety of materials. Furthermore, the invention provides means for measuring the effects of compressive stress on pore volume, pore diameter and pore distribution of through and blind pores. The invention has numerous applications in the development, manufacture and analysis of hydrophobic porous materials that are widely used in many industries, including the fuel cell industry as components of fuel cells, the pharmaceutical industry, healthcare industry, fiber and clothing industry, and filtration media industry, as well as many others.

It is to be understood that the architectural and operational embodiments described herein are exemplary of a plurality of possible arrangements to provide the same (or equivalent) general features, characteristics, and general system operation. Therefore, while there have been described the currently preferred embodiments of the present invention, those skilled in the art will recognize that other and further modifications may be made, without departing from the spirit of the present invention, and it is intended to claim all modifications and variations as fall within the scope of the appended claims. Accordingly, it must further be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. Apparatus for analysis of pore structure characteristics of porous materials, comprising:
    a) a sample chamber having a corrugated bottom and a closure or lid including sealing means for creating a pressure-tight seal between said sample chamber and said closure or lid;
    b) sample holding means within said sample chamber, comprising top and bottom opposing rigid plates;
    c) a penetrometer operably connected to said sample chamber, said penetrometer including a water reservoir and means for measuring a change in volume of said water;
    d) means for supplying an inert gas at an adjustable controlled pressure for pressurization of water within said penetrometer;
    e) vacuum means for creating a partial vacuum within said sample chamber, penetrometer and storage vessel.

2. The apparatus of claim 1, further comprising compression means for accurately applying compressive stress on said sample.

3. The apparatus of claim 2, wherein said compression means comprises a rod operably connected at a first end thereof to said top rigid plate, said rod passing through a pressure-tight seal in said sample chamber closure or lid.

4. The apparatus of claim 3, wherein said rod is connected at a second end thereof to a piston-cylinder device for applying controlled compressive stress on said sample.

5. The apparatus of claim 4, wherein said piston-cylinder device is pneumatically operated.

6. The apparatus of claim 2, wherein said sample chamber sealing means comprises a screw-on lid having an O-ring seal.

7. The apparatus of claim 2, wherein said means for measuring a change in water volume comprises sensing of displacement of a magnet floating on water in said penetrometer.

8. The apparatus of claim 2, wherein said means for measuring a change in water volume comprises sensing of a change in capacitance of the penetrometer column.

9. A method for determining pore structure characteristics of a hydrophobic porous material, comprising the steps of:
    a) providing an apparatus according to claim 1;
    b) placing a test sample of a porous hydrophobic material between the top and bottom opposing rigid plates containing holes, and placing the bottom plate on the corrugated bottom of the clean sample chamber;
    c) sealing the pressure-tight seal between said sample chamber and said closure or lid;
    d) creating a partial vacuum and evacuating the sample chamber to remove air from the sample chamber;
    e) creating a partial vacuum and evacuating the penetrometer and storage vessel above the water level;
    f) releasing the vacuum in a controlled manner using a vacuum regulator, such that desired sub-atmospheric pressure is applied and water contained in the penetrometer enters the sample chamber and intrudes into the pores of the sample;

g) applying a measured amount of intrusion pressure and measuring the change in volume of water in the penetrometer, such that the intrusion pressure is increased from sub-atmospheric values to pressures much above the atmospheric pressures;

h) determining one or more pore structure characteristics of said sample based on the change in volume of the water in said penetrometer.

10. The method of claim 9, further comprising the step of applying a desired amount of compressive stress on the sample.

11. The method of claim 10, wherein said sample chamber is evacuated to at least 1 torr.

12. The method of claim 10, wherein said penetrometer and water storage vessel are evacuated to at least 20 torr.

13. The method of claim 10, wherein the cumulative pore volume of the test material is calculated as the decrease in the volume of water in the penetrometer.

14. The method of claim 10, wherein the pore diameter is computed using the equation $(P-P_p)=-4\gamma\cos\theta/D$.

15. The method of claim 10, wherein the through pore and blind pore volume distribution is computed using the equation $f_v(\log D)=-dV/d\log D$.

16. The method of claim 10, wherein said change in water volume is measured by sensing of displacement of a magnet floating on water in said penetrometer.

17. The method of claim 10, wherein said change in water volume is measured by sensing of a change in the capacitance of the penetrometer column.

* * * * *